US008183261B2

(12) United States Patent
Nakabayashi

(10) Patent No.: US 8,183,261 B2
(45) Date of Patent: May 22, 2012

(54) MICROORGANISM CONTROL AGENT AND STABILIZING METHOD

(75) Inventor: Masaaki Nakabayashi, Osaka (JP)

(73) Assignee: Japan Envirochemicals, Ltd., Osaka-Shi, Osaka (JP)

( * ) Notice: Subject to any disclaimer, the term of this patent is extended or adjusted under 35 U.S.C. 154(b) by 174 days.

(21) Appl. No.: 12/513,582

(22) PCT Filed: Nov. 13, 2007

(86) PCT No.: PCT/JP2007/072004

§ 371 (c)(1), (2), (4) Date: May 5, 2009

(87) PCT Pub. No.: WO2008/065882

PCT Pub. Date: Jun. 5, 2008

(65) Prior Publication Data

US 2010/0069439 A1 Mar. 18, 2010

(30) Foreign Application Priority Data

Nov. 30, 2006 (JP) ................................ 2006-324308

(51) Int. Cl.
*A01N 43/40* (2006.01)

(52) U.S. Cl. ...................................................... 514/332

(58) Field of Classification Search ................... 514/332
See application file for complete search history.

(56) References Cited

U.S. PATENT DOCUMENTS 5,994,383 A * 11/1999 Dyer et al. .................... 514/390
6,251,381 B1 * 6/2001 Kourai et al. ................ 424/76.1

FOREIGN PATENT DOCUMENTS

| | | | |
|---|---|---|---|
| JP | 10-095773 | A | 4/1998 |
| JP | 10-287566 | A | 10/1998 |
| JP | 2000-159607 | A | 6/2000 |
| JP | 2003-081713 | A | 3/2003 |
| JP | 2003-212706 | A | 7/2003 |
| JP | 2003-292408 | A | 10/2003 |
| JP | 2004-067540 | A | 3/2004 |
| JP | 2004-143061 | A | 5/2004 |
| JP | 2004-143140 | A | 5/2004 |
| JP | 2004-196670 | A | 7/2004 |
| JP | 2004-203843 | A | 7/2004 |
| JP | 2004-217501 | A | 8/2004 |
| JP | 2005-179212 | A | 7/2005 |
| JP | 2005-281147 | A | 10/2005 |
| JP | 2007-039388 | A | 2/2007 |

OTHER PUBLICATIONS

Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2007/072004, Jun. 11, 2009, The International Bureau of WIPO, Geneva, CH.
Notification Concerning Transmittal of International Preliminary Report on Patentability (Form PCT/IB/326), International Preliminary Report on Patentability (Form PCT/IB/373), Written Opinion of the International Search Authority (Form PCT/ISA/237) mailed in corresponding International Patent Application No. PCT/JP2007/072004, Jun. 11, 2009, The International Bureau of WIPO, Geneva, CH.
International Search Report (PCT/ISA210) for PCT/JP2007/072004 (in Japanese), completed Dec. 4, 2007.
Written Opinion (PCT/ISA/237) for PCT/JP2007/072004 (in Japanese), completed Dec. 4, 2007.
Office Action issued on Nov. 22, 2011, in corresponding Japanese Patent Application No. 2006-324308.
Antibiotics Antimicrobial Agent Dictionary, Aug. 22, 1986, vol. 1, No. 1, pp. 79, 82, 112, 120, 152, 193, 197 and 202, Japan Society of Antibiotic and Antimicrobial.
Antibiotics Antimicrobial Agent Dictionary, Aug. 22, 1986, vol. 1, No. 1, pp. 79, 82, 112, 120, 152, 193, 197 and 202, Japan Society of Antibiotic and Antimicrobial with English translations of relevant portions thereof.

* cited by examiner

*Primary Examiner* — Sreeni Padmanabhan
*Assistant Examiner* — Timothy E Betton
(74) *Attorney, Agent, or Firm* — Buchanan Ingersoll & Rooney PC

(57) ABSTRACT

Disclosed is a microorganism control agent containing not less than 1% by weight but less than 10% by weight of N,N'-hexamethylenebis(4-carbamoyl-1-decylpyridinium bromide), not less than 35% by weight but less than 60% by weight of at least one alcohol having 2 or 3 carbon atoms, water and an acid.

6 Claims, No Drawings

MICROORGANISM CONTROL AGENT AND STABILIZING METHOD

TECHNICAL FIELD

The present invention relates to microorganism control agents and bis-quaternary ammonium salt stabilizing methods, and more specifically, to a microorganism control agent used as a control agent for bacteria, fungus, yeast, or algae, and an N,N'-hexamethylene bis(4-carbamoyl-1-decylpyridinium bromide) stabilizing method.

BACKGROUND ART

Conventionally, harmful microorganisms such as bacteria, fungus, yeast, and algae are easy to reproduce in various types of industrial products, thereby causing deterioration of productivity or quality, generation of malodor, or the like. Therefore, in order to control the reproduction of these harmful microorganisms, various microorganism control agents which exhibit antimicrobial, antifungal, antiseptic and antialgal effects are widely used.

As an active ingredient of these microorganism control agents, there has been reported that bis-quaternary ammonium salts such as N,N'-hexamethylene bis(4-carbamoyl-1-decylpyridinium bromide) (hereinafter referred to as HMDP-Br in some cases) have a broad antimicrobial spectrum and exhibit excellent control effect (see, for example, the following Patent Document 1).

Further, since the microorganism control agents having HMDP-Br as an active ingredient usually has low solubility of HMDP-Br in water, it is prepared as a solution dissolved with an organic solvent capable of dissolving HMDP-Br at high concentration.

Patent Document 1: Japanese Unexamined Patent Publication No. 2004-143061

DISCLOSURE OF THE INVENTION

Problems to be Solved

However, in such microorganism control agent prepared in the above manner, HMDP-Br is disadvantageously precipitated during transportation or storage in winter or in cold climate areas.

On the other hand, in the microorganism control agent prepared as above, when the microorganism control agent is heated before use or kept continuously in a heated state, HMDP-Br is decomposed in use of the microorganism control agent.

It is an object of the present invention to provide a microorganism control agent containing not less than 1% by weight but less than 10% by weight of N,N'-hexamethylene bis(4-carbamoyl-1-decylpyridinium bromide), the microorganism control agent having excellent storage stability at low temperature and also having excellent decomposition stability at high temperature, and an N,N'-hexamethylene bis(4-carbamoyl-1-decylpyridinium bromide) stabilizing method.

Means for Solving the Problem

To achieve the above object, the present inventors have found that the microorganism control agent is prepared by dissolving not less than 1% by weight but less than 10% by weight of HMDP-Br in a mixed solvent of water and an alcohol, and adding an acid thereto, thereby obtaining excellent storage stability at low temperature and also obtaining excellent decomposition stability at high temperature. As a result of further intensive studies, the present invention has been completed thereby.

That is to say, the present invention provides:

(1) a microorganism control agent containing not less than 1% by weight but less than 10% by weight of N,N'-hexamethylene bis(4-carbamoyl-1-decylpyridinium bromide); not less than 35% by weight but less than 60% by weight of at least one alcohol having either 2 or 3 carbon atoms; water; and an acid, (2) the microorganism control agent described in (1), in which the acid is an edible organic acid, (3) the microorganism control agent described in (2), in which the edible organic acid is a citric acid, (4) the microorganism control agent described in (1), in which the acid is contained in a range of 0.1 to 40 mol per 1 mol of N,N'-hexamethylene bis(4-carbamoyl-1-decylpyridinium bromide), (5) the microorganism control agent described in (4), in which the acid is contained in a range of 0.1 to 10 mol per 1 mol of N,N'-hexamethylene bis(4-carbamoyl-1-decylpyridinium bromide), and (6) an N,N'-hexamethylene bis(4-carbamoyl-1-decylpyridinium bromide) stabilizing method containing the step of mixing not less than 1% by weight but less than 10% by weight of N,N'-hexamethylene bis(4-carbamoyl-1-decylpyridinium bromide), not less than 35% by weight but less than 60% by weight of at least one alcohol having either 2 or 3 carbon atoms, water, and an acid.

Effect of the Invention

Since the microorganism control agent of the present invention contains an acid, the N,N'-hexamethylene bis(4-carbamoyl-1-decylpyridinium bromide) is stabilized. Specifically, the microorganism control agent has excellent storage stability at low temperature and also has excellent decomposition stability at high temperature. Therefore, stable transportation and storage of the microorganism control agent at low temperature can be reliably achieved, and stable use thereof at high temperature can also be securely ensured.

According to the N,N'-hexamethylene bis(4-carbamoyl-1-decylpyridinium bromide) stabilizing method of the present invention, the storage stability of N,N'-hexamethylene bis(4-carbamoyl-1-decylpyridinium bromide) at low temperature can be improved and the decomposition stability thereof at high temperature can also be improved.

EMBODIMENT OF THE INVENTION

The microorganism control agent of the present invention contains N,N'-hexamethylene bis(4-carbamoyl-1-decylpyridinium bromide), at least one alcohol having either 2 or 3 carbon atoms, water, and an acid.

In the present invention, N,N'-hexamethylene bis(4-carbamoyl-1-decylpyridinium bromide) (hereinafter referred to as HMDP-Br) is an active ingredient of the microorganism control agent, and is a bis-quaternary ammonium salt represented by the following formula (1):

[Chem. 1]

(1)

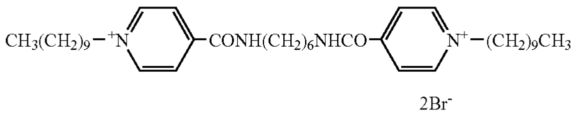

The HMDP-Br can be produced by a known method (e.g., the method described in Japanese Unexamined Patent Publication No. 9-110692 or Japanese Unexamined Patent Publication No. 10-95773) or a method analogous to the method. Alternatively, commercially available products can be used. Examples of the commercially available product include Dimer38 (trade name, manufactured by Inui Corporation, Japan).

In the present invention, examples of the at least one alcohol having either 2 or 3 carbon atoms (hereinafter referred to as C2-3 alcohol) include monohydric alcohols such as ethanol, 1-propanol, and 2-propanol. These C2-3 alcohols can be used alone or in combination of two or more kinds. From the viewpoint of safety, ethanol is preferable.

In the present invention, the acid is not particularly limited as long as it is an acid soluble in a mixed solvent of water and the C2-3 alcohol, and includes organic acids and inorganic acids.

Examples of the organic acid include edible organic acids such as citric acid, lactic acid, acetic acid, propionic acid, butyric acid, succinic acid, adipic acid, malic acid, tartaric acid, gluconic acid, oxalic acid, fumaric acid, sorbic acid, benzoic acid, malonic acid, and p-oxybenzoic acid; and non-edible organic acids such as formic acid, trifluoroacetic acid, and maleic acid.

Examples of the inorganic acid include hydrochloric acid, nitric acid, sulfuric acid, and phosphoric acid.

Among these acids, from the viewpoint of corrosiveness to metals, an organic acid is preferable, or from the viewpoint of safety, an edible organic acid is more preferable, or a citric acid is even more preferable.

Although the microorganism control agent of the present invention can be used containing, for example, not less than 10% by weight of HMDP-Br, it preferably contains not less than 1% by weight but less than 10% by weight of HMDP-Br. When the content ratio of the HMDP-Br is not less than 10% by weight, the use (storage and handling) of the microorganism control agent is limited in accordance with the provisions of the law (e.g., the Fire Service Law, etc.), which is inconvenient. On the other hand, when it is less than 1% by weight, the control effect of the HMDP-Br cannot be sufficiently exhibited.

Although the microorganism control agent of the present invention can be used containing, for example, not less than 30% by weight but not more than 80% by weight of the C2-3 alcohol, it preferably contains not less than 35% by weight but less than 60% by weight of the C2-3 alcohol. When the content ratio of the C2-3 alcohol exceeds 60% by weight, the use (storage and handling) of the microorganism control agent is limited in accordance with the provisions of the law (e.g., the Fire Service Law, etc.), which is inconvenient. On the other hand, when it is less than 35% by weight, the storage stability of the microorganism control agent at low temperature is deteriorated.

The acid is contained in an amount of 0.1 to 40 mol, preferably 0.1 to 10 mol, or more preferably 0.1 to 5 mol, per 1 mol of HMDP-Br (molecular weight: 768.76). When the content of the acid exceeds the above-mentioned range, it may be disadvantageous from the viewpoint of cost, and the microorganism control agent may have a higher viscosity, thereby causing difficulties in handling. On the other hand, when it is less than the above-mentioned range, the decomposition stability of the microorganism control agent at high temperature may be deteriorated.

The water content corresponds to the remainder (of the whole) relative to the content of each of the above ingredients.

In the microorganism control agent of the present invention, there can be added known additives such as other active ingredients, surfactant, antioxidant, and light stabilizer, as long as the advantageous effect of the present invention is not impaired.

When the total content of the ingredients other than water and the C2-C3 alcohol, i.e., the total content of the HMDP-Br, the acid, and the additive is not less than 10% by weight, the use (storage and handling) of the microorganism control agent is limited in accordance with the provisions of the law (e.g., the Fire Service Law, etc.), which is inconvenient.

Thus, the microorganism control agent of the present invention is prepared in a liquid form as described above, it can subsequently be formulated in various preparation forms such as suspensions, pastes, powders, granules, and microcapsules. Alternatively, the microorganism control agent may be prepared in an inclusion form and can further be formulated by supporting the agent on montmorillonite (smectite, etc.) such as a layered silicate, or by adsorbing the agent to clay, silica, white carbon, or talc.

The microorganism control agent of the present invention is prepared by mixing an acid with an alcoholic aqueous solution containing HMDP-Br, C2-3 alcohol, and water at the above-mentioned content ratio. In addition, a known additive can also be mixed simultaneously with, or before and after the mixing of the above-mentioned acid.

HMDP-Br can be stabilized by the preparation of the microorganism control agent.

The microorganism control agent of the present invention can be effectively used in applications where harmful microorganisms are controlled, including various industrial water from paper-pulp mills and cooling water circulation system; metal processing oils such as cutting oil; and various industrial products such as casein, starch paste, glue, coated paper, coating liquid for papers, surface sizing agent, paint, adhesive, synthetic rubber latex, ink, polyvinyl alcohol film, vinyl chloride film, resin product, cement admixture, sealing agent, and joint mixture.

Specifically, the microorganism control agent is preferably used as a harmful microorganism control agent for industrial use, such as slime control agent used in paper-pulp mills, antiseptic agent in metal processing oils, antiseptic/antifungal agent in paints, antiseptic/antifungal agent in resin emulsions, antiseptics in cement admixtures, antiseptic/antifungal agent in inks, antiseptic/antifungal agent in dampening water, antiseptic/antifungal agent in cement water reducing agents, and life prolonging agent for plants.

In particular, in the microorganism control agent of the present invention, the above-mentioned HMDP-Br is stabilized, and specifically, storage stability of the HMDP-Br at low temperature can be improved, and decomposition stability thereof at high temperature can also be improved.

Therefore, the microorganism control agent with the HMDP-Br thus stabilized can reliably achieve stable transportation and storage at low temperature in winter or in cold climate areas.

Moreover, stable use thereof at high temperature can also be securely ensured.

The amount of the microorganism control agent of the present invention may be appropriately determined according to the object to be applied. However, for example, when used as an antiseptic, antifungal, or antialgal agent, the microorganism control agent can be diluted to a concentration of 10 to 5000 mg (total active ingredients)/kg (product), or preferably 100 to 4000 mg (total active ingredients)/kg (product), or for example, when used as a bactericide (antimicrobial agent), the microorganism control agent can be diluted to a concentration of 10 to 5000 mg (total active ingredients)/kg (diluent solvent (e.g., water)), or preferably 100 to 4000 mg (total active ingredients)/kg (diluent solvent).

EXAMPLES

The present invention will now be described in more detail by way of Examples and Comparative Examples.

(Preparation of Microorganism Control Agent)

Example 1

A solution was prepared by mixing 40 g (52 mmol) of N,N'-hexamethylene bis(4-carbamoyl-1-decylpyridinium bromide) (HMDP-Br, Dimer38, manufactured by Inui Corporation, Japan), 540 g of an ethanol, and 410 g of water, and dissolving the mixture by stirring. Then, 10 g (52 mmol) of a citric acid was mixed therewith and the resulting mixture was dissolved by stirring, to thereby prepare 1000 g of a microorganism control agent.

Example 2

In the same manner as in Example 1, 1000 g of a microorganism control agent was prepared except that 4.7 g (52 mmol) of a lactic acid was used in place of 10 g (52 mmol) of the citric acid, and 415.3 g of water was used in place of 410 g of water.

Example 3

In the same manner as in Example 1, 1000 g of a microorganism control agent was prepared except that 3.1 g (52 mmol) of an acetic acid was used in place of 10 g (52 mmol) of the citric acid, and 416.9 g of water was used in place of 410 g of water.

Example 4

In the same manner as in Example 1, 1000 g of a microorganism control agent was prepared except that 6.0 g (52 mmol) of a fumaric acid was used in place of 10 g (52 mmol) of the citric acid, and 414 g of water was used in place of 410 g of water.

Example 5

In the same manner as in Example 1, 1000 g of a microorganism control agent was prepared except that 6.0 g (52 mmol) of a maleic acid was used in place of 10 g (52 mmol) of the citric acid, and 414 g of water was used in place of 410 g of water.

Example 6

In the same manner as in Example 1, 1000 g of a microorganism control agent was prepared except that 1.9 g (52 mmol) of a hydrochloric acid was used in place of 10 g (52 mmol) of the citric acid, and 418.1 g of water was used in place of 410 g of water.

Comparative Example 1

In the same manner as in Example 1, 1000 g of a microorganism control agent was prepared except that the citric acid was not mixed, and 420 g of water was used in place of 410 g of water.

Example 7

In the same manner as in Example 1, 1000 g of a microorganism control agent was prepared except that 540 g of 1-propanol was used in place of 540 g of the ethanol.

Example 8

In the same manner as in Example 1, 1000 g of a microorganism control agent was prepared except that 540 g of 2-propanol was used in place of 540 g of the ethanol.

Comparative Example 2

In the same manner as in Example 1, 1000 g of a microorganism control agent was prepared except that 540 g of a methanol was used in place of 540 g of the ethanol.

Example 9

A solution was prepared by mixing 10 g (13.0 mmol) of N,N'-hexamethylene bis(4-carbamoyl-1-decylpyridinium bromide) (HMDP-Br, Dimer38, manufactured by Inui Corporation), 540 g of an ethanol, and 447.5 g of water, and dissolving the mixture by stirring. Then, 2.5 g (13.0 mmol) of a citric acid was mixed therewith and the resulting mixture was dissolved by stirring, to thereby prepare 1000 g of a microorganism control agent.

Example 10

In the same manner as in Example 9, 1000 g of a microorganism control agent was prepared except that 590 g of an ethanol was used in place of 540 g of the ethanol, and 397.5 g of water was used in place of 447.5 g of water. Example 11

In the same manner as in Example 9, 1000 g of a microorganism control agent was prepared except that 350 g of an ethanol was used in place of 540 g of the ethanol, and 637.5 g of water was used in place of 447.5 g of water.

Comparative Example 3

In the same manner as in Example 9, 1000 g of a microorganism control agent was prepared except that 300 g of an ethanol was used in place of 540 g of the ethanol, and 687.5 g of water was used in place of 447.5 g of water.

Example 12

In the same manner as in Example 1, 1000 g of a microorganism control agent was prepared except that 50 g (260 mmol) of a citric acid was used in place of 10 g (52 mmol) of the citric acid, and 370 g of water was used in place of 410 g of water.

Example 13

In the same manner as in Example 1, 1000 g of a microorganism control agent was prepared except that 1 g (5.2 mmol)

of a citric acid was used in place of 10 g (52 mmol) of the citric acid, and 419 g of water was used in place of 410 g of water.

Example 14

In the same manner as in Example 9, 1000 g of a microorganism control agent was prepared except that 46.8 g (520 mmol) of a lactic acid was used in place of 2.5 g (13.0 mmol) of the citric acid, and 403.2 g of water was used in place of 447.5 g of water.

Example 15

In the same manner as in Example 1, 1000 g of a microorganism control agent was prepared except that 0.1g (0.52 mmol) of a citric acid was used in place of 10 g (52 mmol) of the citric acid, and 419.9 g of water was used in place of 410 g of water.

Example 16

In the same manner as in Example 1, 1000 g of a microorganism control agent was prepared except that 95 g (124 mmol) of HMDP-Br was used in place of 40 g (52 mmol) of the HMDP-Br, 362.6 g of water was used in place of 410 g of water, and 2.4 g (12.4 mmol) of a citric acid was used in place of 10 g (52 mmol) of the citric acid.

(Evaluation of Microorganism Control Agent)

(1) Storage Stability at Low Temperature

The microorganism control agent prepared in each of Examples and Comparative Examples was supplied into a sealed vessel, and stored at 10° C. for a month. The microorganism control agent after the storage was visually observed to confirm the presence or absence of precipitation of HMDP-Br. The storage stability at low temperature was evaluated thereby. The results are shown in Table 1. In Table 1, "A" represents the absence of precipitation of HMDP-Br, and "B" represents the presence of precipitation of HMDP-Br.

(2) Decomposition Stability at High Temperature

The microorganism control agent prepared in each of Examples and Comparative Examples was diluted with water so that the concentration of HMDP-Br was 1000 ppm. Thereafter, the diluted agent was supplied into a sealed vessel, and stored at 80° C. for a month. The residual ratio of HMDP-Br after the storage was measured by high performance liquid chromatography to evaluate decomposition stability at high temperature. The results are shown in Table 1.

TABLE 1

| Components | | | | Molecular Weight | | Ex. 1 | Ex. 2 | Ex. 3 | Ex. 4 | Ex. 5 | Ex. 6 | Comp. Ex. 1 | Ex. 7 | Ex. 8 | Comp. Ex. 2 |
|---|---|---|---|---|---|---|---|---|---|---|---|---|---|---|---|
| Components of Microorganism Control Agent | | HMDP-Br (Dimer38) | | 768.8 | Content | 4 | 4 | 4 | 4 | 4 | 4 | 4 | 4 | 4 | 4 |
| | Alcohol | (C2-C3) | Ethanol | — | Ratio | 54 | 54 | 54 | 54 | 54 | 54 | 54 | — | — | — |
| | | | 1-Propanol | | (wt %) | — | — | — | — | — | — | — | 54 | — | — |
| | | | 2-Propanol | | | — | — | — | — | — | — | — | — | 54 | — |
| | | (C1) | Methanol | | | — | — | — | — | — | — | — | — | — | 54 |
| | | Water | | | | 41 | 41.53 | 41.69 | 41.4 | 41.4 | 41.81 | 42 | 41 | 41 | 41 |
| | Acid | Edible Organic Acid | Citric Acid | 192.1 | | 1 | — | — | — | — | — | — | 1 | 1 | 1 |
| | | | Lactic Acid | 90.1 | | — | 0.47 | — | — | — | — | — | — | — | — |
| | | | Acetic Acid | 60 | | — | — | 0.31 | — | — | — | — | — | — | — |
| | | | Fumaric Acid | 116 | | — | — | — | 0.60 | — | — | — | — | — | — |
| | | Non-edible Organic Acid | Maleic Acid | 116 | | — | — | — | — | 0.60 | — | — | — | — | — |
| | | Inorganic Acid | Hydrochloric Acid | 36.46 | | — | — | — | — | — | 0.19 | — | — | — | — |
| | | (mol) (per 1 mole of HMDP-Br) | | | | 1 | 1 | 1 | 1 | 1 | 1 | 0 | 1 | 1 | 1 |
| Evaluation of Microorganism Control Agent | Storage Stability (10° C., one month) | | Presence/Absence of Precipitation of HMDP-Br | | | A | A | A | A | A | A | A | A | A | B |
| | Decomposition Stability* (80° C., one month) | | Residual Ratio of HMDP-Br | | % | 99 | 99 | 98 | 99 | 98 | 99 | 47 | 99 | 99 | 95.4 |

| Components | | | | Molecular Weight | | Ex. 9 | Ex. 10 | Ex. 11 | Comp. Ex. 3 | Ex. 12 | Ex. 13 | Ex. 14 | Ex. 15 | Ex. 16 |
|---|---|---|---|---|---|---|---|---|---|---|---|---|---|---|
| Components of Microorganism Control Agent | | HMDP-Br (Dimer38) | | 768.8 | Content | 1 | 1 | 1 | 1 | 4 | 4 | 1 | 4 | 9.5 |
| | Alcohol | (C2-C3) | Ethanol | — | Ratio | 54 | 59 | 35 | 30 | 54 | 54 | 54 | 54 | 54 |
| | | | 1-Propanol | | (wt %) | — | — | — | — | — | — | — | — | — |
| | | | 2-Propanol | | | — | — | — | — | — | — | — | — | — |
| | | (C1) | Methanol | | | — | — | — | — | — | — | — | — | — |
| | | Water | | | | 44.75 | 39.75 | 63.75 | 68.75 | 37 | 41.9 | 40.32 | 41.99 | 36.26 |
| | Acid | Edible Organic Acid | Citric Acid | 192.1 | | 0.25 | 0.25 | 0.25 | 0.25 | 5 | 0.1 | — | 0.01 | 0.24 |
| | | | Lactic Acid | 90.1 | | — | — | — | — | — | — | 4.68 | — | — |
| | | | Acetic Acid | 60 | | — | — | — | — | — | — | — | — | — |
| | | | Fumaric Acid | 116 | | — | — | — | — | — | — | — | — | — |
| | | Non-edible | Maleic Acid | 116 | | — | — | — | — | — | — | — | — | — |

TABLE 1-continued

| | | | | | | | | | | | | |
|---|---|---|---|---|---|---|---|---|---|---|---|---|
| | Organic Acid | | | | | | | | | | | |
| | Inorganic Acid | Hydrochloric Acid | 36.46 | — | — | — | — | — | — | — | — | — |
| | (mol) (per 1 mole of HMDP-Br) | | | 1 | 1 | 1 | 1 | 5 | 0.1 | 40 | 0.01 | 0.1 |
| Evaluation of Microorganism Control Agent | Storage Stability (10° C., one month) | Presence/Absence of Precipitation of HMDP-Br | | A | A | A | B | A | A | A | A | A |
| | Decomposition Stability* (80° C., one month) | Residual Ratio of HMDP-Br | % | 100 | 99 | 99 | 100 | 99.9 | 97.1 | 100 | 52.8 | 99 |

Decomposition Stability*: Solution diluted with water so that the concentration of HMDP-Br is 1000 ppm.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The microorganism control agent of the present invention can be used as an agent having excellent storage stability in stable transportation and storage at low temperature in winter or in cold climate areas, and also having excellent decomposition stability in stable use at high temperature.

The invention claimed is:

1. A microorganism control agent comprising:

not less than 1% by weight but less than 10% by weight of N,N'-hexamethylene bis(4-carbamoyl-1-decylpyridinium bromide);

not less than 35% by weight but less than 60% by weight of at least one monohydric alcohol having either 2 or 3 carbon atoms;

water; and an acid.

2. The microorganism control agent according to claim 1, wherein the acid is an edible organic acid.

3. The microorganism control agent according to claim 2, wherein the edible organic acid is a citric acid.

4. The microorganism control agent according to claim 1, wherein the acid is contained in a range of 0.1 to 40 mol per 1 mol of N,N'-hexamethylene bis(4-carbamoyl-1-decylpyridinium bromide).

5. The microorganism control agent according to claim 4, wherein the acid is contained in a range of 0.1 to 10 mol per 1 mol of N,N'-hexamethylene bis(4-carbamoyl-1-decylpyridinium bromide).

6. An N,N'-hexamethylene bis(4-carbamoyl-1-decylpyridinium bromide) stabilizing method comprising mixing not less than 1% by weight but less than 10% by weight of N,N'-hexamethylene bis(4-carbamoyl-1-decylpyridinium bromide), not less than 35% by weight but less than 60% by weight of at least one monohydric alcohol having either 2 or 3 carbon atoms, water, and an acid.

* * * * *